(12) United States Patent
Tyner et al.

(10) Patent No.: US 12,251,483 B2
(45) Date of Patent: Mar. 18, 2025

(54) GLIDING ARC DISCHARGE STERILIZATION OF SURFACES, OBJECTS, AND AMBIENT AIR

(71) Applicant: APJeT, Inc., Morrisville, NC (US)

(72) Inventors: David W. Tyner, Benson, NC (US); Gregory A. Roche, Durham, NC (US); Preston A. Roche, Chapel Hill, NC (US)

(73) Assignee: APJeT, Inc., Morrisville, NC (US)

( * ) Notice: Subject to any disclaimer, the term of this patent is extended or adjusted under 35 U.S.C. 154(b) by 620 days.

(21) Appl. No.: 17/508,747

(22) Filed: Oct. 22, 2021

(65) Prior Publication Data

US 2022/0125971 A1   Apr. 28, 2022

Related U.S. Application Data

(60) Provisional application No. 63/105,046, filed on Oct. 23, 2020.

(51) Int. Cl.
*A61L 2/14*   (2006.01)
*A61L 9/22*   (2006.01)

(52) U.S. Cl.
CPC ............ *A61L 2/14* (2013.01); *A61L 9/22* (2013.01); *A61L 2202/121* (2013.01); *A61L 2202/122* (2013.01); *A61L 2202/15* (2013.01); *A61L 2202/17* (2013.01); *A61L 2209/134* (2013.01); *A61L 2209/14* (2013.01)

(58) Field of Classification Search
CPC ..................................... A61L 2/14; A61L 9/22
See application file for complete search history.

(56) References Cited

FOREIGN PATENT DOCUMENTS

KR   20120097139 A   *   9/2012

OTHER PUBLICATIONS

English Translation of Document Identification No. KR 20120097139 A provided by the Korean Intellectual Property Office website KIPO: Yoon Bong Han; High-Efficiency Gliding Arc Reactor; Sep. 3, 2012 (Year: 2012).*

Joanna Pawlat, Piotr Terebun, Michal Kwlatkowski, Barbora Tarabova, Zuzana Kovalova, Katarina Kucerova, Zdenko Machala, Mario Janda, Karol Hensel, Evaluation of Oxidative Species in Gaseous and Liquid Phase Generated by Mini-Gliding Arc Discharge, Plasma Chemistry and Plasma Processing (2019) 39:627-642, Mar. 28, 2019.

* cited by examiner

*Primary Examiner* — Kevin Joyner
(74) *Attorney, Agent, or Firm* — Samuel M. Freund; Cochran Freund & Young LLC

(57) ABSTRACT

Apparatus for sterilizing surfaces and apparatus for sterilizing air and enclosed objects using gliding arc discharge technology are described, whereby disinfecting products formed in the discharge are prevented from escaping from the apparatus into the ambient air.

5 Claims, 12 Drawing Sheets

FIG. 6C

GLIDING ARC DISCHARGE STERILIZATION OF SURFACES, OBJECTS, AND AMBIENT AIR

CROSS-REFERENCE TO RELATED APPLICATIONS

The present application claims the benefit of U.S. Provisional Patent Application No. 63/105,046 for "Gliding Arc Discharge Sterilization Of Surfaces, Objects, And Ambient Air" that was filed on 23 Oct. 2020, the entire content of which Patent Application is hereby specifically incorporated by reference herein for all that it discloses and teaches.

BACKGROUND

Cold atmospheric plasmas operating at close to room temperature have been shown to be useful for decontamination of heat-sensitive substrates. An advantage of plasmas over UV-based disinfection systems is that plasmas are not limited by shadowing effects. However, unlike the efficacy of UV-C for killing viruses on dry samples, that for plasmas is significantly reduced.

Nonthermal or cold (nonequilibrium) atmospheric plasmas generated in air in the presence of water vapor produce various radicals and reactive molecules called reactive oxygen and nitrogen species (RONS), and include hydroxyl radicals, OH, hydrogen peroxide, $H_2O_2$, nitrogen oxides, $N_2O$, NO, $NO_2$, ozone, $O_3$, and superoxide, $O_2^{*-}$, as examples.

The gliding arc discharge is an electrical discharge formed between at least two divergent electrodes powered by a high-voltage power supply and having a plasma gas flowing between the electrodes. The discharge initiates with an arc at the shortest gap between the electrodes, after which it elongates and travels along the diverging path between the electrodes as a result of gas flow transverse to the discharge. Since the elongating discharge requires more power to remain operational in order to compensate for losses resulting from the increasing volume of the plasma, the plasma will extinguish, and the system will await another discharge initiation in the ignition region.

Gliding arc discharges operate at atmospheric pressure and have high plasma density and power. The generated plasmas are weakly ionized and lack local thermodynamic equilibrium since the electron energy is much higher than that of the heavy plasma species; they are generally classified as non-thermal plasmas. Operating with humid air as the plasma gas, the species generated include: $NO^-$, $OH^-$, $N_2^+$, and $O_2^+$, and the nitrogen oxides, NO, $NO_2^+$, $NO_3^+$, and ONOOH.

Gliding arc discharges have been used to decontaminate bacteria present in aqueous and phosphate buffered solutions disposed below the electrodes, where the nitrogen oxides have generated high concentrations of nitrites and nitrates therein.

SUMMARY

In accordance with the purposes of the present invention, as embodied and broadly described herein, an embodiment of the apparatus for surface sterilization hereof, includes: a first planar electrode having a chosen thickness and a straight edge having a chosen length, a first end, and a second end; a second planar electrode having a chosen thickness, and a straight edge having a chosen length, a first end, and a second end, the straight edge of the second electrode opposing the straight edge of the first electrode, being spaced-apart and divergent therefrom, with the first end of the first electrode disposed a chosen distance from the first end of the second electrode, and the second end of the first electrode disposed at a larger distance away from the second end of the second electrode; a high-voltage power source in electrical connection between the first electrode and the second electrode for providing a high voltage to the first electrode; an air blower for providing a flow of air between the straight edge of the first electrode and the opposing straight edge of the second electrode; an outer, air-tight chamber for enclosing the air blower, the outer chamber having an interior volume and one side with a flat portion, such that a first area of the flat portion is open and close to or in contact with the surface; and an inner chamber disposed in the interior volume of the outer chamber for enclosing the first electrode and the second electrode, and having one side with a flat portion, such that a second area of the flat portion is open and close to or in contact with the surface within the first area; whereby, air is circulated by the air blower from the interior volume of the outer chamber into the inner chamber, and a gliding arc plasma is generated near the first end of the straight edge of the first electrode and the first end of the straight edge of the second electrode by the high-voltage provided by the high-voltage power source, which moves between the straight edge of the first electrode and the opposing straight edge of the second electrode until it extinguishes, thereby increasing the concentration of products formed in the plasma.

In another aspect of the present invention and in accordance with the purposes thereof, as embodied and broadly described herein, an embodiment of the apparatus for surface sterilization hereof, includes: at least one first planar electrode having a chosen thickness and a straight edge having a chosen length, a first end, and a second end; a cylindrical second electrode having a chosen diameter, a chosen length, an outer surface, a first end, and a second end, the outer surface of the second electrode opposing the straight edge of the at least one first electrode, being spaced-apart and divergent therefrom, with the first end of the at least one first electrode disposed a chosen distance from the outer surface of the first end of the second electrode, and the second end of the at least one first electrode disposed at a larger distance away from the outer surface of the second end of the second electrode; a high-voltage power source in electrical connection between the at least one first electrode and the second electrode for providing a high voltage to the at least one first electrode; an air blower for providing a flow of air between the straight edge of the at least one first electrode and the opposing outer surface of the second electrode; an outer, air-tight chamber for enclosing the air blower, the outer chamber having an interior volume and one side with a flat portion, such that a first area of the flat portion is open and close to or in contact with the surface; and an inner chamber disposed in the interior volume of the outer chamber for enclosing the at least one first electrode and the second electrode, and having one side with a flat portion, such that a second area of the flat portion is open and close to or in contact with the surface within the first area; whereby, air is circulated by the air blower from the interior volume of the outer chamber into the inner chamber, and a gliding arc plasma is generated near the first end of the straight edge of the at least one first electrode and the outer surface of the first end of the second electrode by the high-voltage provided by the high-voltage power source, which moves between the straight edge of the at least one first electrode and the opposing outer surface of the second electrode until it extinguishes, thereby increasing the concentration of products formed in the plasma.

In yet another aspect of the present invention and in accordance with the purposes thereof, as embodied and broadly described herein, an embodiment of the apparatus for air sterilization hereof, includes: at least one first planar electrode having a chosen thickness and a straight edge having a chosen length, a first end, and a second end; at least one second planar electrode having a chosen thickness, and a straight edge having a chosen length, a first end, and a second end, the straight edge of the at least one second electrode opposing the straight edge of the at least one first electrode, being spaced-apart and divergent therefrom, with the first end of the at least one first electrode disposed a chosen distance from the first end of the at least one second electrode, and the second end of the at least one first electrode disposed at a larger distance away from the second end of the at least one second electrode; a first high-voltage power source in electrical connection between the at least one first electrode and the at least one second electrode for providing a high voltage to the at least one first electrode; an air-tight chamber for enclosing the at least one first electrode and the at least one second electrode, the chamber having an air inlet and an air outlet and an internal volume; a fan disposed outside of the internal volume of the chamber for drawing air through the internal volume and out of the chamber through the air outlet thereof, and between the at least one first electrode and the at least one second electrode; whereby, a first gliding arc plasma is generated near the first end of the straight edge of the first electrode and the first end of the straight edge of the second electrode by the high-voltage provided by the first high-voltage power source, which moves between the straight edge of the first electrode and the opposing straight edge of the second electrode until it extinguishes; and a filter element disposed outside of the internal volume of the chamber between the chamber and the fan effective for removing products formed in the plasma.

In still another aspect of the present invention and in accordance with the purposes thereof, as embodied and broadly described herein, an embodiment of the apparatus for air sterilization hereof, includes: at least one first planar electrode having a chosen thickness and a straight edge having a chosen length, a first end, and a second end; at least one second planar electrode having a chosen thickness, and a straight edge having a chosen length, a first end, and a second end, the straight edge of the at least one second electrode opposing the straight edge of the at least one first electrode, being spaced-apart and divergent therefrom, with the first end of the at least one first electrode disposed a chosen distance from the first end of the at least one second electrode, and the second end of the at least one first electrode disposed at a larger distance away from the second end of the at least one second electrode; a high-voltage power source in electrical connection between the at least one first electrode and the at least one second electrode for providing a high voltage to the at least one first electrode; at least one air blower for providing a flow of air between the straight edge of the at least one first electrode and the opposing outer surface of the at least one second electrode; whereby, a gliding arc plasma is generated near the first end of the straight edge of the first electrode and the first end of the straight edge of the second electrode by the high-voltage provided by the high-voltage power source, which moves between the straight edge of the first electrode and the opposing straight edge of the second electrode until it extinguishes; a chamber for enclosing the at least one first electrode and the at least one second electrode, and the at least one blower, the chamber having an air inlet and an air outlet and an internal volume; a plate for supporting the at least one first electrode, the at least one second electrode, and the at least one blower, the plate having a first side facing the air inlet of the chamber, and a second side upon which the at least one first electrode, the at least one second electrode, and the at least one blower are supported; a fan disposed outside of the internal volume of the chamber for drawing air through the internal volume and out of the chamber through the air outlet thereof; a baffle parallel to and disposed a chosen distance from the second side of the plate for creating turbulence in the vicinity of the generated gliding arc plasma; and a filter element disposed in the internal volume of the chamber for removing products formed in the gliding arc plasma.

Benefits and advantages of the present invention include, but are not limited to, providing apparatus for sterilizing surfaces and objects, and apparatus for sterilizing air using gliding arc discharge technology, whereby disinfecting products formed in the discharge are increased in concentration to improve effectiveness of sterilization, and also prevented from escaping from the apparatus into the ambient air.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings:

FIG. 3C is a schematic representation of a bottom view of the plasma discharges generated by the apparatus of FIG. 3A, illustrating 8 plasma discharges with a discharge circle diameter of about 1.5 in. with the full circle diameter being about 3 in.

FIG. 6C is a schematic representation of an embodiment of the apparatus shown in FIG. 6B hereof used for determining the effectiveness of the air sterilizer.

DETAILED DESCRIPTION

Figure 1B:
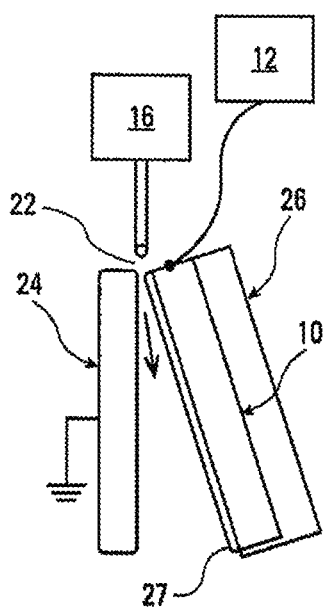
FIG. 1B is a schematic representation of another embodiment of electrodes effective for generating a gliding arc discharge, illustrating a cylindrical common ground electrode used with at least two powered electrodes as used in FIGS. 3A-3C and FIGS. 4A-4D, hereof.

Briefly, the present invention includes apparatus for sterilizing surfaces and objects, and apparatus for sterilizing air using gliding arc discharge technology, whereby disinfecting products formed in the discharge are prevented from escaping from the apparatus into the ambient air.

Reference will now be made in detail to the present embodiments of the invention, examples of which are illustrated in the accompanying drawings. In the Figures, similar structure will be identified using identical reference characters. It will be understood that the FIGURES are presented for the purpose of describing particular embodiments of the invention and are not intended to limit the invention thereto.

Figure 1A:
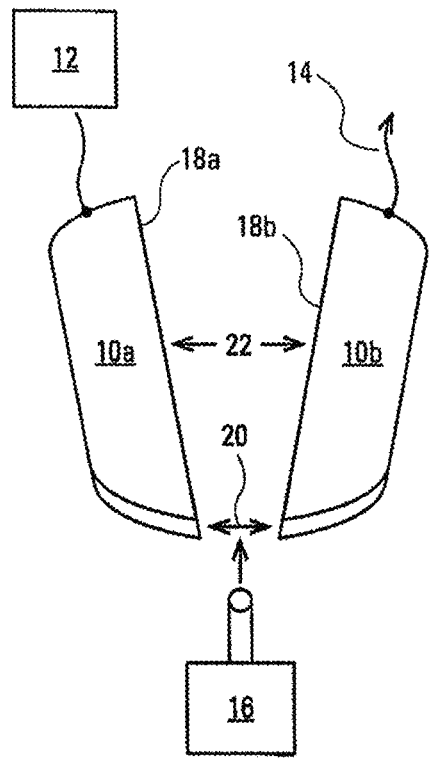
FIG. 1A is a schematic representation of an embodiment of a pair of divergent electrodes effective for generating a gliding arc discharge.

Turning now to FIG. 1A a schematic representation of an embodiment of a pair of divergent planar electrodes, 10a, and 10b, effective for generating a gliding arc discharge, when powered by high-voltage source, 12, are shown. Electrical lead, 14, can either be grounded or connected to high-voltage source 12 to complete the circuit, depending on the type of high-voltage source employed. Supports for electrodes 10a and 10b are not shown in FIG. 1A, but many types of supports are envisioned. Air blower, 16, directs air between flat faces, 18a, and 18b, of electrodes 10a and 10b. Air flow rates between 20 and 80 liters/min. were used. The discharge is initiated at the narrowest distance, 20, between the electrodes and progresses down the electrode spacing, 22, until conditions no longer permit a discharge to occur between electrodes 10a and 10b.

FIG. 1B is a schematic representation of another embodiment of electrodes effective for generating a gliding arc discharge, illustrating cylindrical common ground electrode, 24, employed with at least two powered electrodes 10, arranged in a divergent orientation around ground electrode 24, one of which is shown attached to electrically insulating cone, 26, which may be made of ceramic materials or machinable $NO_3$ inert materials such as Kynar or PEEK. The powered electrodes or blades 10 would be mounted in slots in insulating cone 26, to where they are disposed slightly (between about 1 mm and 2 mm) beyond the inside surface, 27, of cone 26. As will be shown and described in FIGS. 3A-3C and FIGS. 4A-4D, below, multiple gliding arc discharge configurations may be envisioned.

Cylindrical ground electrode 24 would have a nominal diameter of about ¼", in a range between about 8 mm and 12 mm, a nominal length of about 35 mm in a range between about 20 mm and 50 mm, and rounded edges. Distance 22 is nominally about 4 mm in a range between about 3 mm and 5 mm, (the closest distance between powered electrodes 10 and to ground electrode 24), with a nominal distance of about 11 mm in a range between about 9 mm and 15 mm as the furthest distance therefrom. Nominal lengths of blades 10 for this plasma source would be 35 mm in a range between about 20 mm and 50 mm.

Figure 1C:
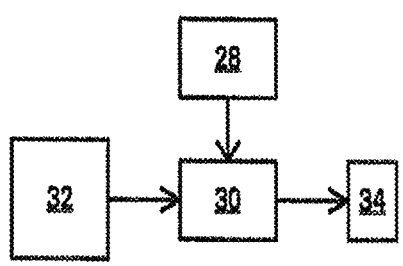
FIG. 1C shows an electrical block diagram of a coil on plug system for powering an automobile ignition coil driver suitable for generating a gliding arc discharge.
Figure 1D:
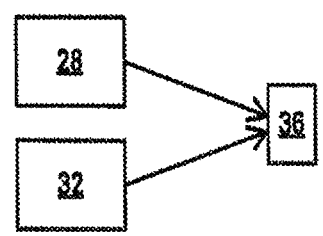
FIG. 1D shows an electrical block diagram of another coil on plug system for powering an automobile ignition coil driver suitable for generating a gliding arc discharge.

FIGS. 1C and 1D show electrical block diagrams of two embodiments of systems for powering an automobile ignition coils effective for generating a gliding arc discharge. In FIG. 1C, an automobile ignition coil driver for a "dumb" coil-on-plug is illustrated. Function generator, 28, provides the shape and duration of each pulse, driving switching module, 30, powered by 12 V supply, 32, with TTL signals, which causes coil, 34, in electrical connection with a powered electrode in a gliding arc discharge configuration shown in FIGS. 1A and 1B hereof to discharge, there being one coil 34 connected to each powered electrode. The output of switching module 30 is a pulse between about 4 V and 12 V. If several powered electrodes are employed, one wire to each coil from switching module 30 is used. FIG. 1D shows an automobile ignition coil driver for a "smart" coil-on-plug. Again, function generator 28 provides the shape and duration of each pulse, this time driving coil, 36, powered by 12 V supply 32, directly, since 5 V logic signals from function generator 28 now provides switching instructions to "smart" coil 36.

Pulse power sources initially used for the gliding arc discharges of embodiments of the present invention were developed for and widely used for powering neon signs, since they are inexpensive, ubiquitous, and meet UL and other safety standards. Most of these sources operate at 110 V, but some may be operated using 12 V power supplies, but only deliver a maximum of about 12 kV to the plasma.

Another disadvantage of such power supplies is that they cannot be located closer than about 2 in. between units, since they interact electrically and can shut down unexpectedly.

As stated above, the off-the-shelf automotive "coil-on-plug" (COP) ignition components used for initiating the gliding arc discharges employed in embodiments of the present invention operate with a pulsed 12 V DC signal provided to a high-voltage coil mounted directly on engine spark plugs, for automotive use, but in direct electrical contact with the powered electrodes hereof. The compact coils permit 8 gliding arc plasmas to occupy the same area as 2 of the neon sign power sources. The COP components are capable of delivering 30 kV-40 kV to the plasmas, depending on the coil, versus at most 12 kV for the neon sign power sources. The COP components can also be operated at lower voltages, including 12 kV, if desired. Such higher voltages are expected to generate increased numbers and types of plasma products effective for sterilization of surfaces and air. As an example, water will break down at about 25 kV. The voltage waveform is adjustable for each COP independently of the others, which will permit the breakdown voltage for each plasma discharge to be adjusted for variations due to electrode blade alignment. Additionally, plasma uniformity and density can also be controlled, as well as power density for heat management of the electrode blades. Some COP coils provide real-time ignition feedback signals which allows for diagnosis of the discharge.

Figure 2:
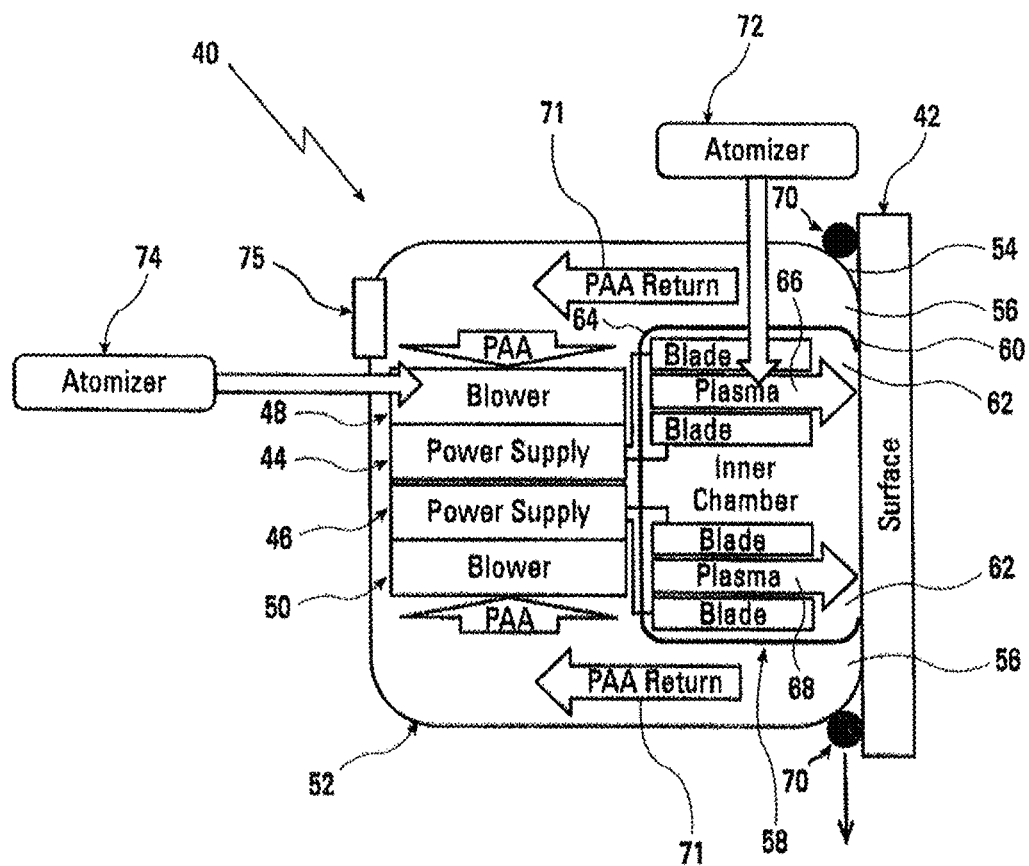
FIG. 2 is a schematic representation of the side view of an embodiment gliding arc plasma apparatus for decontaminating a surface, showing two plasma generators, and illustrating recirculation of the plasma activated species through the plasmas for increasing activated species concentrations and the use of an atomizer for introducing water into the plasmas.

FIG. 2 is a schematic representation of the side view of an embodiment gliding arc plasma apparatus, 40, for decontaminating surface, 42, showing two plasma generators, 44, and 46, using the electrode configuration illustrated in FIG. 1A, above, and blowers, 48, and 50, enclosed in air-tight chamber, 52, having flat side, 54, a portion, 56, of which is open to surface 42. Chamber 52 also encloses inner chamber, 58, also having flat side, 60, a portion, 62, of which is open to surface 42, and having openings in opposing side or wall, 64, for permitting blowers 48 and 50 to direct air into plasmas, 66, and 68, of plasma generators 44 and 46, respectively, and out of inner chamber 58 through opening 62. Gasket, 70, prevents the plasma products from escaping from apparatus 40 as the apparatus is moved along surface 42 by directing the unused plasma products into opening 56 of chamber 52, thereby recirculating plasma-activated air (PAA), 71, through blowers 48 and 50 and again through plasmas 66 and 68 for increasing activated species concentrations. This configuration slightly pressurizes inner chamber 58 relative to outer chamber 52. Atomizers, 72, and 74, are employed for introducing water into plasmas 66 and 68, respectively, either directly or through blowers 48 and 50, or both. Evacuation fan/filter, 75, is triggered in the event that gliding arc discharge apparatus 40 is removed from surface 42, or if one or more plasma discharge products exceeds a predetermined level in chamber 52.

Clearly, additional plasma generators 44 and 46 can be employed in apparatus 40, as needed. Additionally, surface 42 can be moved relative to chamber 52, or the chamber moved relative to the surface, depending on the situation encountered.

Figure 3A:
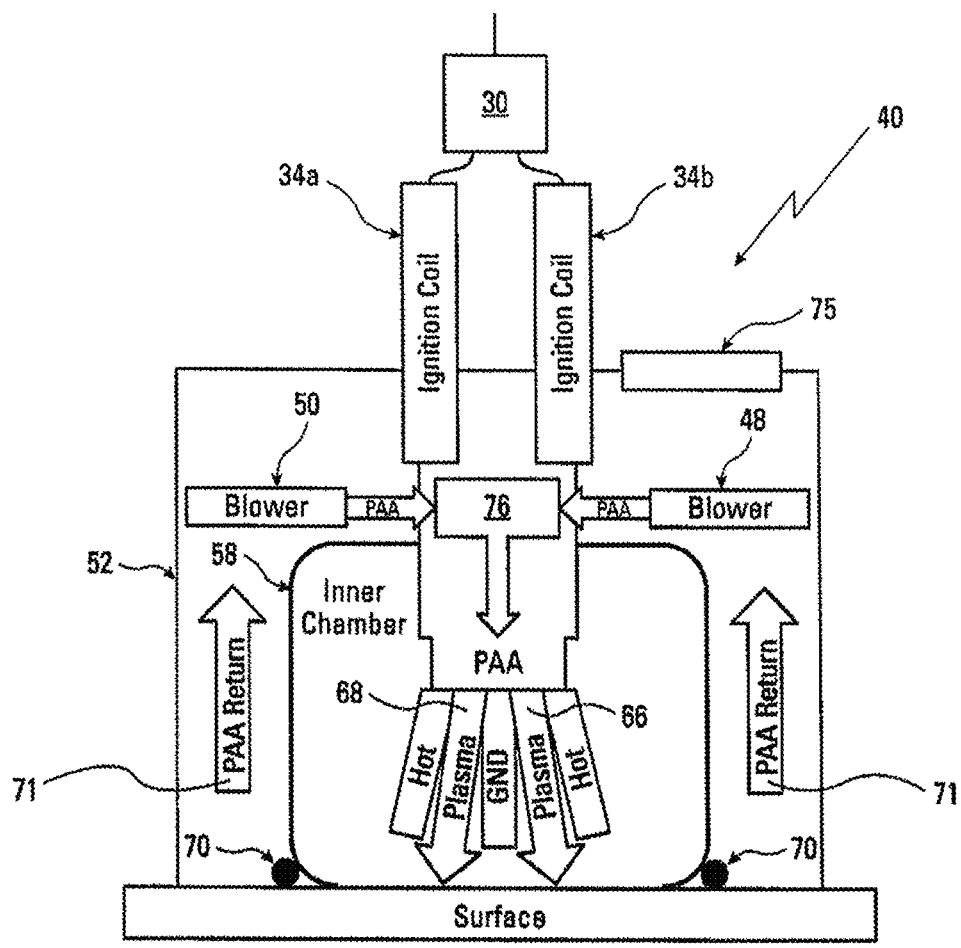
FIG. 3A is a schematic representation of side view of an embodiment of a gliding arc plasma apparatus for decontaminating a surface using automobile ignition coils for powering the plasma, where several electrode blades can share a common ground when disposed in a circular configuration, as illustrated in FIG. 1B hereof.

FIG. 3A is a schematic representation of side view of an embodiment of a gliding arc plasma apparatus 40 for decontaminating surface 42 where several electrode blades can share a common ground when disposed in a circular configuration, as illustrated in FIG. 1B hereof. Automobile ignition coils 34 are illustrated as being used for powering plasmas 66 and 68. Blowers 48 and 50 are shown circulating PAA through T-fitting, 76, inserted through wall 64 of inner chamber 52 which directs the PAA through the plasmas, thereby increasing the concentrations of plasma activated species.

Figure 3B:
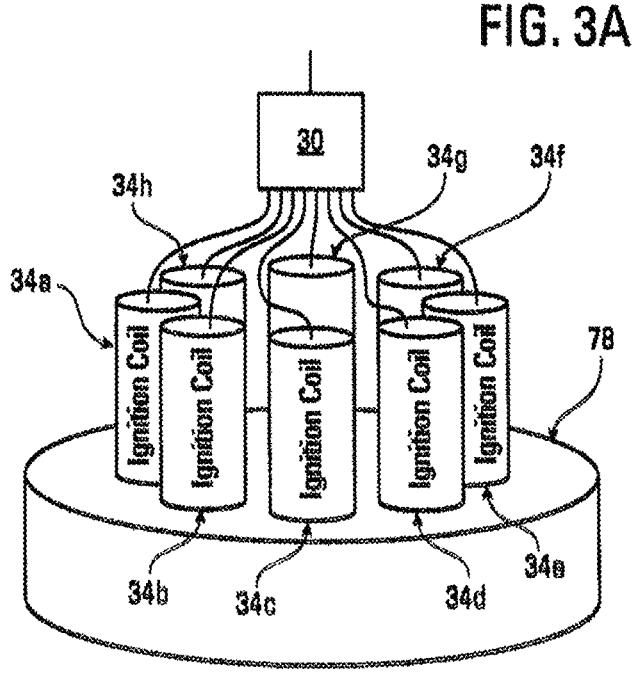
FIG. 3B is a schematic representation of a perspective side view of the gliding arc discharges shown in FIG. 3A.
Figure 3C:
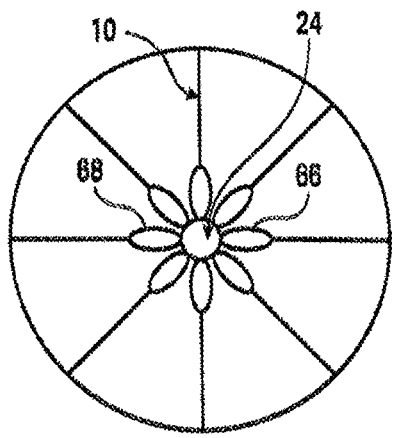

FIG. 3B is a schematic representation of a side perspective view of the gliding arc plasmas shown in FIG. 3A. Eight ignition coils 34 supported by insulating block, 78, are illustrated, each powering a blade electrode sharing a common ground electrode 24, with each ignition coil separately powered by switching module 30 in FIG. 1B. FIG. 3C is a schematic representation of a bottom view of the plasma discharges generated by the apparatus of FIG. 3A.

Figure 4B:
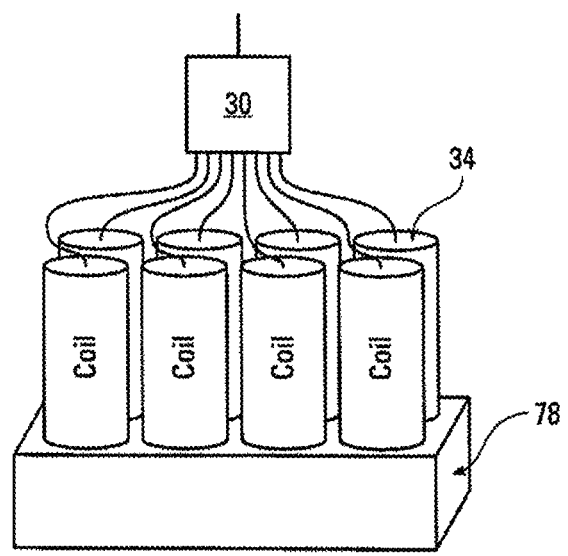
FIG. 4B is a schematic representation of a perspective side view of a linear configuration of pairs of opposing, powered electrodes shown in FIG. 4A.
Figure 4C:
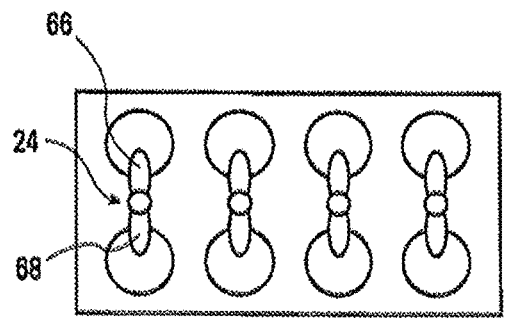
FIG. 4C is a schematic representation of the plasmas formed by the gliding arc discharge configuration of FIG. 4B.
Figure 4A:
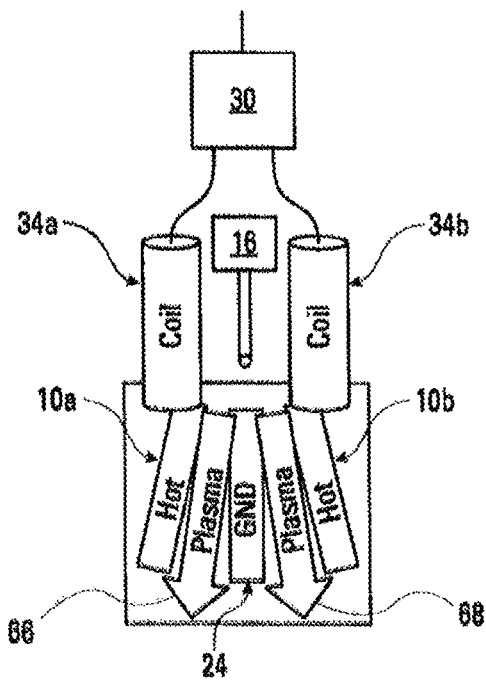
FIG. 4A is a schematic representation of a side view of another configuration of gliding arc discharges effective for decontaminating a surface using automobile ignition coils for powering plasmas, where at two opposing, powered electrode blades share common cylindrical ground therebetween.

FIG. 4A is a schematic representation of a side view of another configuration of the gliding arc discharges effective for decontaminating a surface using automobile ignition coils 34a and 34b for powering plasmas 66 and 68, where two opposing, powered electrode blades 10a and 10b share common cylindrical ground 24 therebetween. FIG. 4B is a schematic representation of a perspective side view of a linear configuration of pairs of opposing, powered electrodes shown in FIG. 4A, suitable for use in embodiments of gliding arc discharge apparatus 40 for decontaminating surface 42; and FIG. 4C is a schematic representation of the plasmas 66 and 68 formed by the gliding arc discharge configuration of FIG. 4B.

Figure 5:
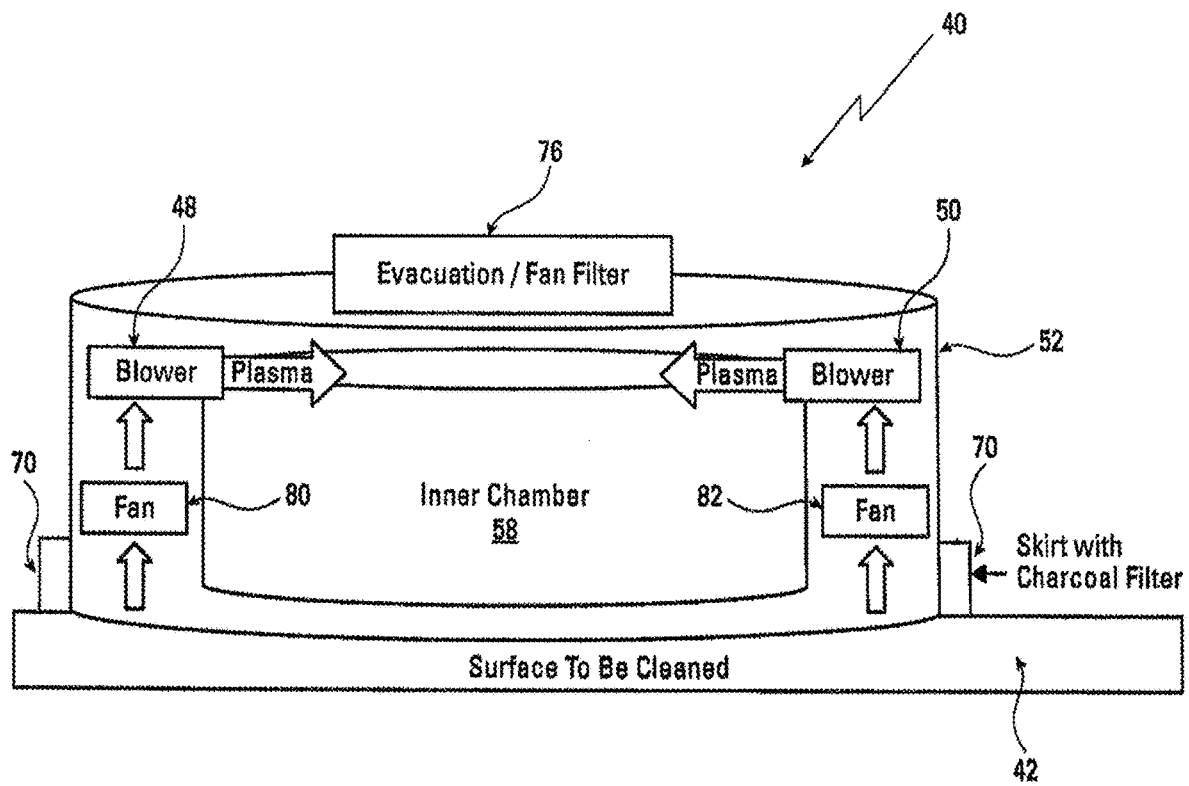
FIG. 5 is a schematic representation of another embodiment of the gliding arc discharge apparatus of the present invention for decontaminating a large surface, illustrating the use of extra fans to maintain circulation of the plasma activated air into the chamber after contacting the surface, thereby increasing the concentration of plasma generated species, and illustrating an evacuation fan/filter is used to evacuate the chamber and the inner chamber after the decontamination process has been completed or if the concentration of nitrogen oxides exceeds a chosen level.

FIG. 5 is a schematic representation of another embodiment of gliding arc discharge apparatus 40 of the present invention for decontaminating a large surface, illustrating the use of extra fans, 80, and 82, to maintain circulation of the plasma activated air into the chamber after contacting surface 42, thereby increasing the concentration of plasma generated species, and illustrating evacuation fan/filter 76 used to evacuate chamber 52 and the inner chamber 58 after the decontamination process has been completed, or if the concentration of nitrogen oxides exceeds a chosen level. Gliding arc discharge generators shown in FIG. 1A or 1B, or a combination thereof, may be used for this embodiment, which is anticipated to be useful as a robotic, "vacuum cleaner" style apparatus. As in the embodiments illustrated in FIGS. 2 and 3A hereof, the plasma may either be in contact with or in close proximity with surface 42.

Figure 6A:
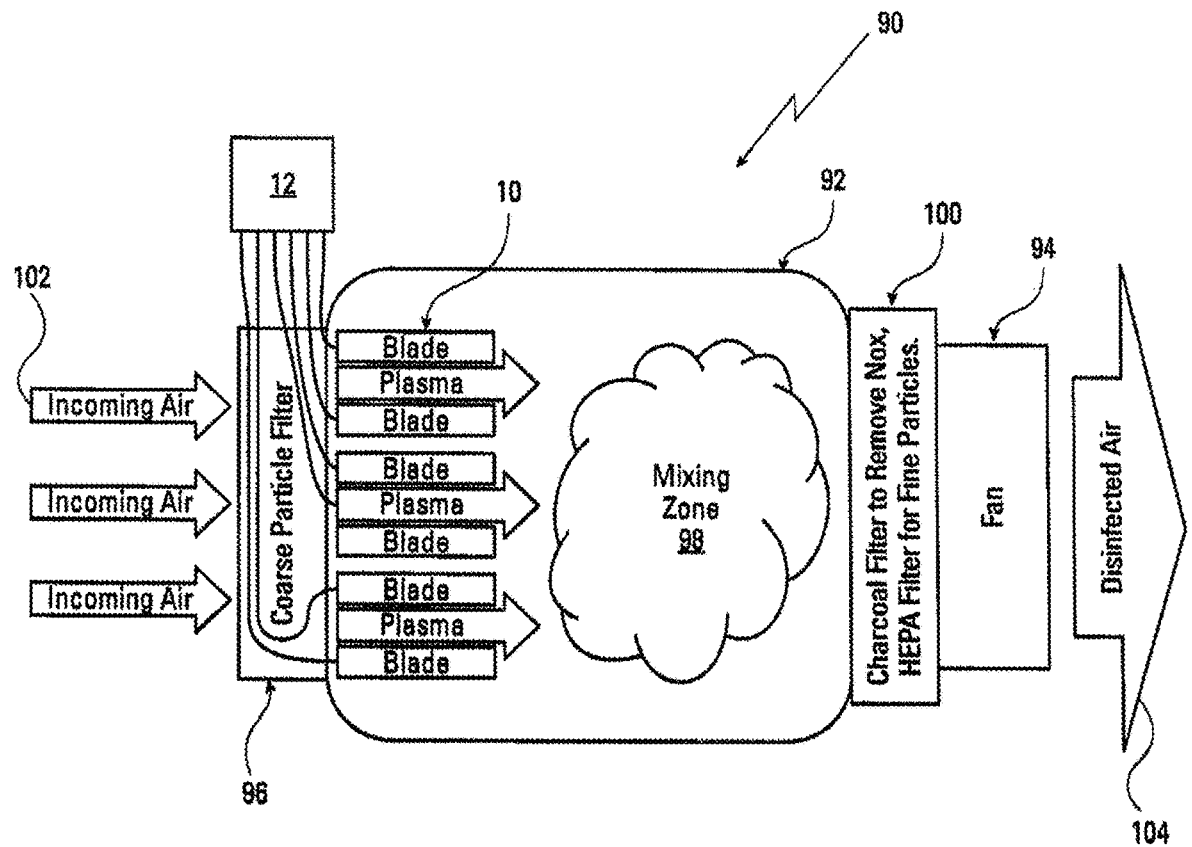
FIG. 6A is a schematic representation of the side view of an air purifier embodiment of the present invention, illustrating a chamber containing a plurality of gliding arc discharges through which filtered air is drawn, the disinfected air then being filtered to remove the plasma-generated species.

FIG. 6A is a schematic representation of the side view of air purifier embodiment, 90, of the present invention, illustrating first chamber, 92, containing a plurality of gliding arc discharges in blades 10 powered by power supply 12, through which air is drawn by fan, 94, through filter, 96, plasma activated air generated in gliding arc discharges 10 then mixes with any air already in or introduced into chamber 92 in mixing zone, 98, which is then directed into charcoal or carbon filter, 100, to remove the plasma-generated species. In embodiments of air purifier 90, all of incoming air, 102, is shown passing through the discharges; however, additional air inlets which do not direct the air into the discharges, but into mixing zone 98 before leaving chamber 92 as disinfected air, 104, are envisioned. It should be mentioned that either of the gliding arc discharge apparatus illustrated in FIGS. 1A and 1B and combinations thereof can be used in air purifier 90 in numbers necessary to handle the desired air flow.

Figure 6B:
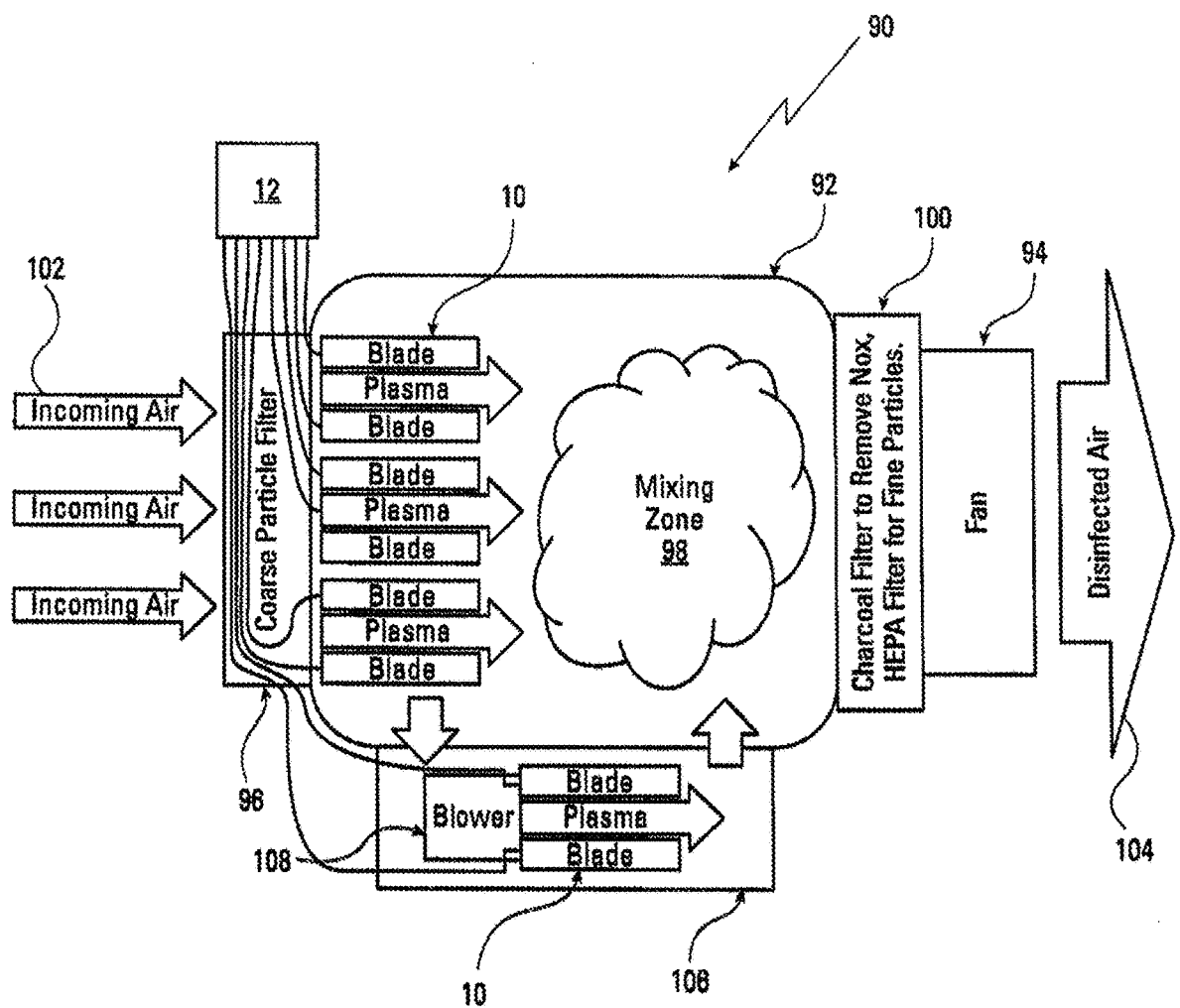
FIG. 6B is a schematic representation of the side view of the air purifier shown in FIG. 6A having a second chamber containing at least one gliding arc discharge through which air from the first chamber is directed in order to increase the concentration of plasma-activated species.

FIG. 6B is a schematic representation of the side view of the air purifier shown in FIG. 6A, illustrating air from chamber 92 being directed by blower, 108, into smaller second chamber, 106, containing at least one pair of gliding arc discharge electrodes 10 powered by high-voltage power supply 12, in order to increase the concentration of plasma-activated species. Either of the gliding arc discharge apparatus illustrated in FIGS. 1A and 1B and combinations thereof can be used in air purifier 90, in numbers necessary to handle the desired air flow.

Figure 6C:
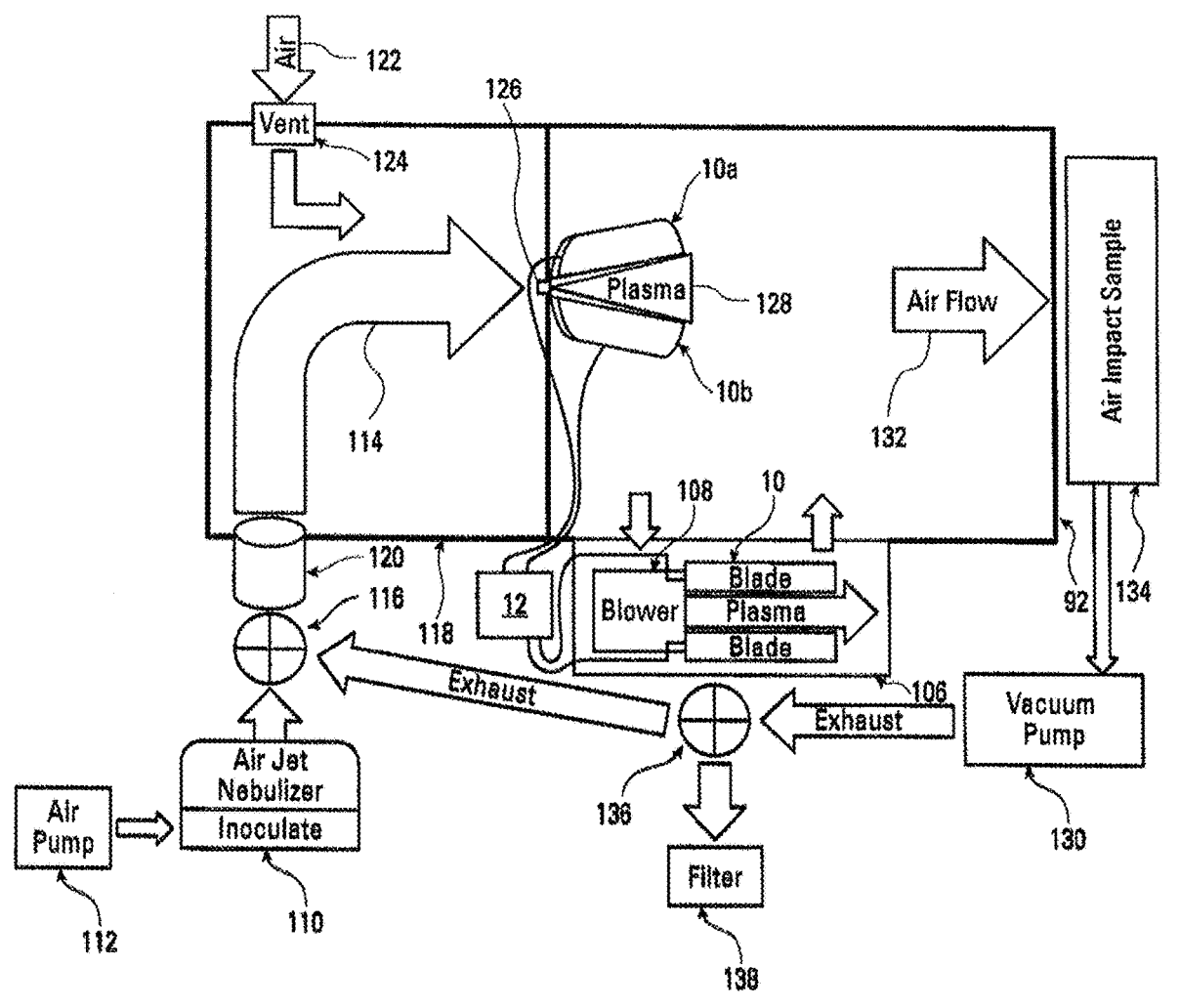

FIG. 6C is a schematic representation of an embodiment of the apparatus shown in FIG. 6B hereof used for determining the effectiveness of the air sterilizer. Air is pumped into air jet nebulizer, 110, by air pump, 112, forming mist of inoculate, 114, which passes through 3-way valve, 116, into mist chamber, 118, through port, 120. Outside air, 122, entering chamber 118 through vent, 124, mixes with mist 114 to form a uniform aerosolization of inoculate, and enters chamber 92 through holes, 126, before passing through 4 discharge electrode pairs 10a, 10b powered by high-voltage power supply 12, forming thereby 4 gliding arc discharge plasmas, 128 (Primary Plasma). Vacuum pump, 130, pumps the mixture of air with the inoculate mist, 132, through air impact sampler or monitor, 134, containing an agar plate, which absorbs airborne microbes from the air passing therethrough, where it is exhausted through 3-way valve, 136, into filter, 138, or back into mist chamber 118 through 3-way valve 116 through port 120. Air from chamber 92 is directed by blower, 108 into smaller chamber, 106, containing at least one pair of gliding arc discharge electrodes 10 powered by high-voltage power supply 12, in order to increase the concentration of plasma-activated species, and/or for use for self-cleaning the system by being directed into chamber 118 through valves 136 and 116 and port 120.

Figure 7:
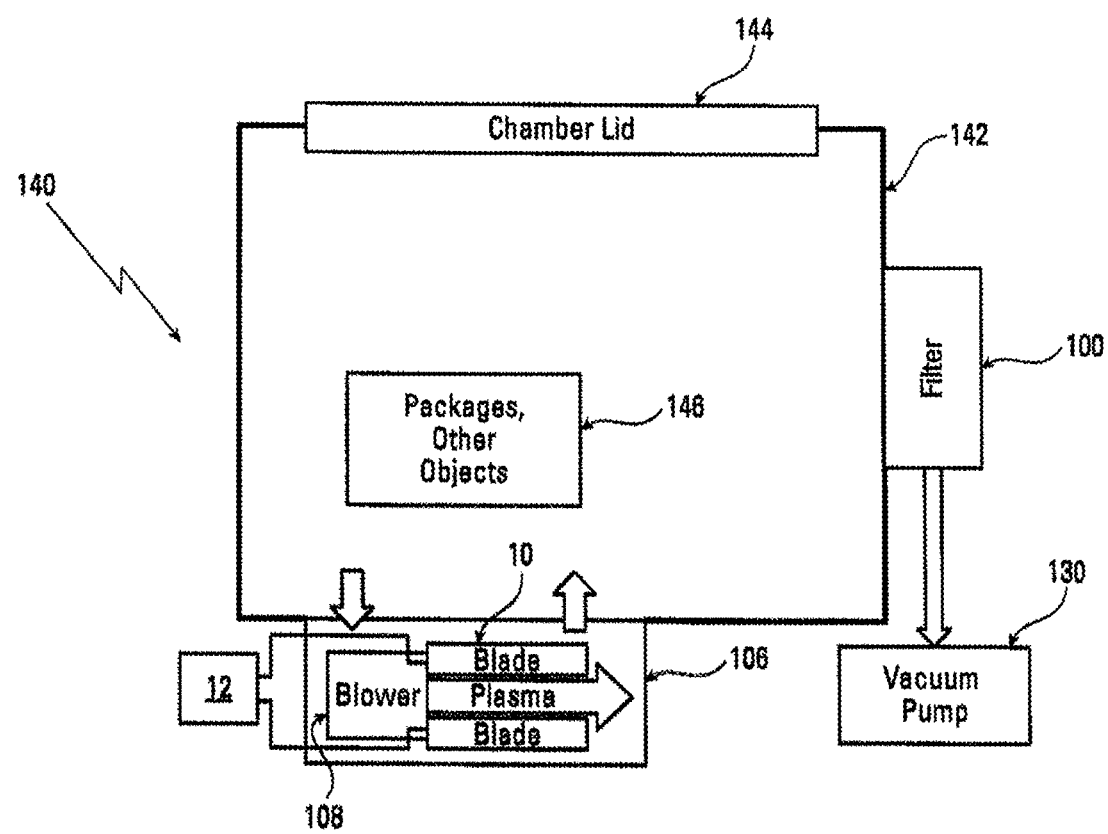
FIG. 7 is a schematic representation of a side view of an object disinfectant embodiment of the present invention, illustrating an air-tight object enclosure, having a lid for inserting an object to be disinfected, and a second chamber in fluid contact with the object enclosure for directing air from the object enclosure through a gliding arc discharge and returning plasma-generated species and air to the object enclosure using a blower.

FIG. 7 is a schematic representation of a side view of object disinfectant embodiment, 140, of the present invention, illustrating air-tight object enclosure, 142, having sealing lid, 144, for inserting object, 146, to be disinfected, and second chamber 106 in fluid contact with object enclosure 142 for directing air from the object enclosure through gliding arc discharge electrode plates 10 powered by high-voltage power supply 12, whereby a plasma is formed therebetween, and returning plasma-generated species and air to the object enclosure using blower 108. Once lid 144 is closed, no air is admitted to object enclosure 142, except for that circulated through chamber 106, which originates in object enclosure 142. Objects 146 may include packages, personal protective equipment, and the like. In operation, the blower/plasma combination recirculate the plasma air, thereby raising the NO concentration to an estimated 6000 ppm in about 30 min., thereby creating a strong disinfecting environment for the enclosed objects. Experiments have shown a 99.9% reduction in Staphylococcus aureus in 30 s, and 99.99% reduction in 60 s. After disinfection is completed, the NO is drawn through charcoal filter 100 by vacuum pump 130 to remove all of the NON.

It was found by detailed examination of the embodiment illustrated in FIG. 6 hereof that with the gliding arc discharge apparatus utilized without a blower, but with the electrodes suspended in the air stream, that 0.2 ppm of $NO_2$ was generated; that, if a blower was used in the same air stream under the electrodes, that 0.8 ppm of $NO_2$ was generated, and that, if a blower with a baffle were used in the same air stream, 1.2 ppm of $NO_2$ was generated. Thus, air disinfection device 150 was developed over purification embodiment 90 in FIG. 6.

Figure 8A:
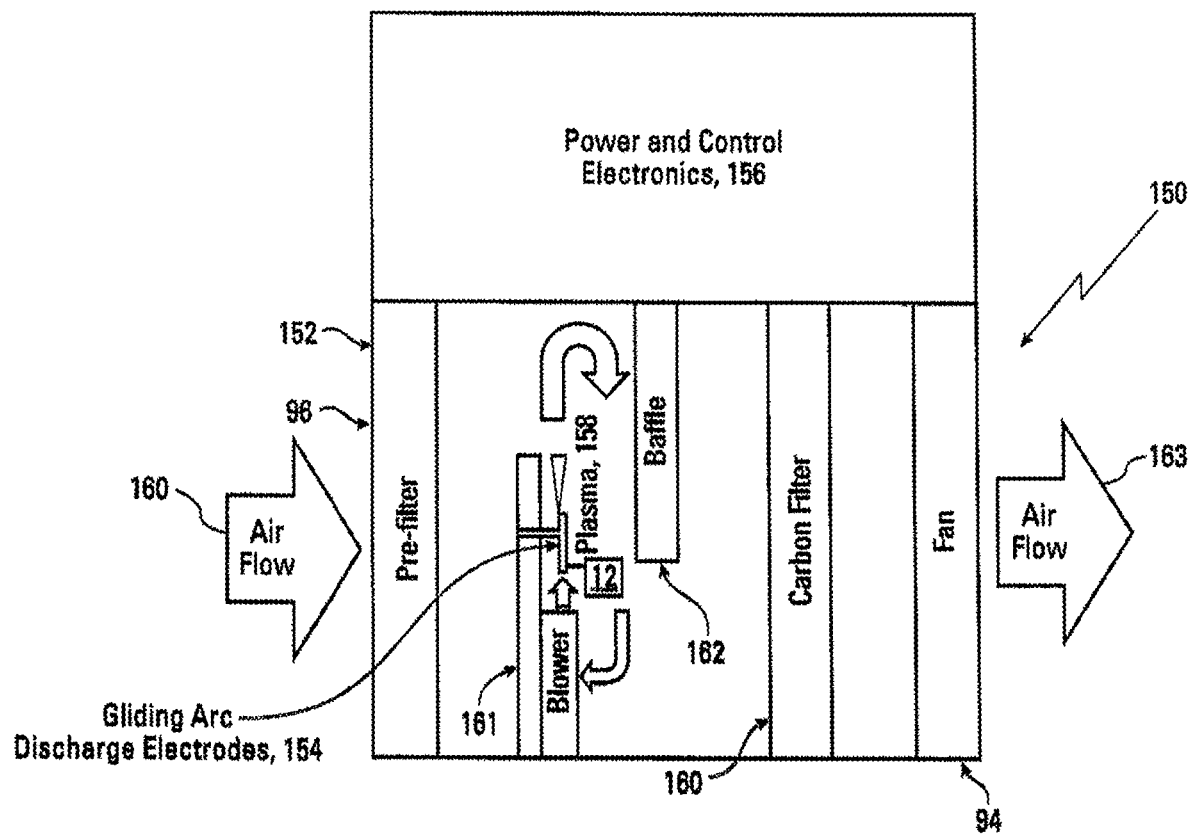
FIG. 8A is a schematic representation of the side view of another air disinfectant embodiment of the present invention, illustrating a chamber containing at least one gliding arc discharge device through which filtered air is drawn, the disinfected air then being filtered to remove the plasma-generated species.
Figure 8B:
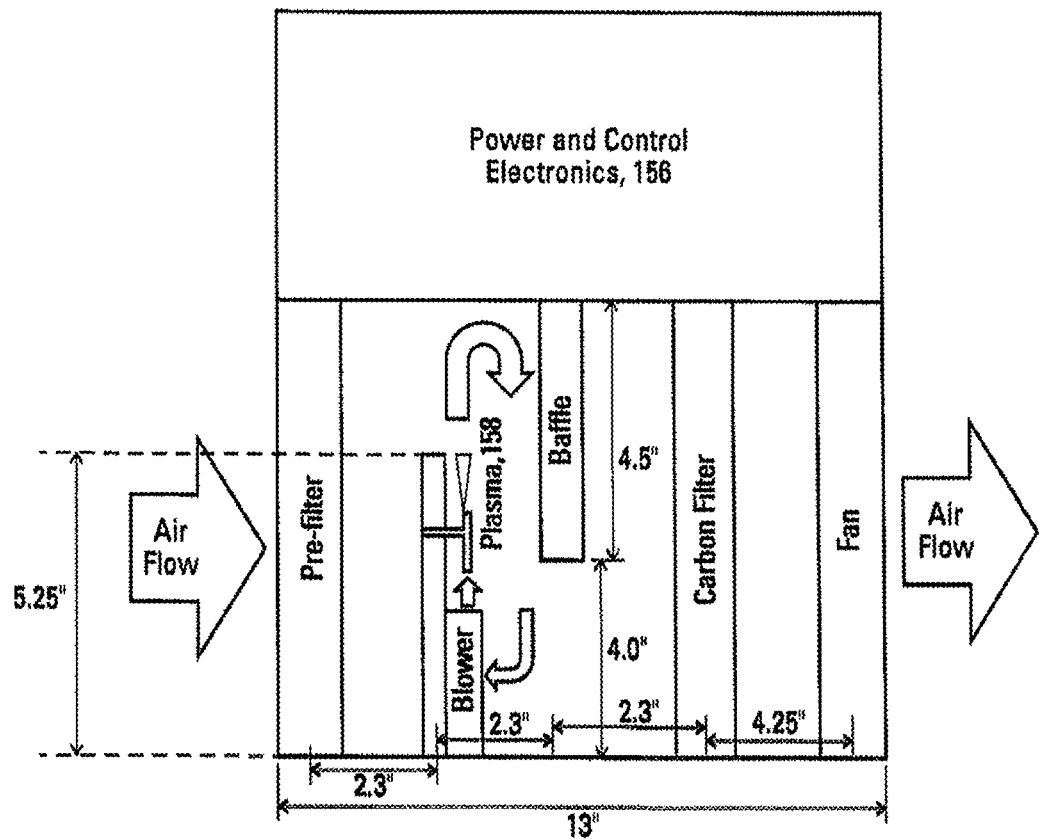
FIG. 8B is a schematic representation of the side view of the air disinfectant embodiment of the present invention shown in FIG. 8A hereof, illustrating some dimensions of the apparatus as built.
Figure 8C:
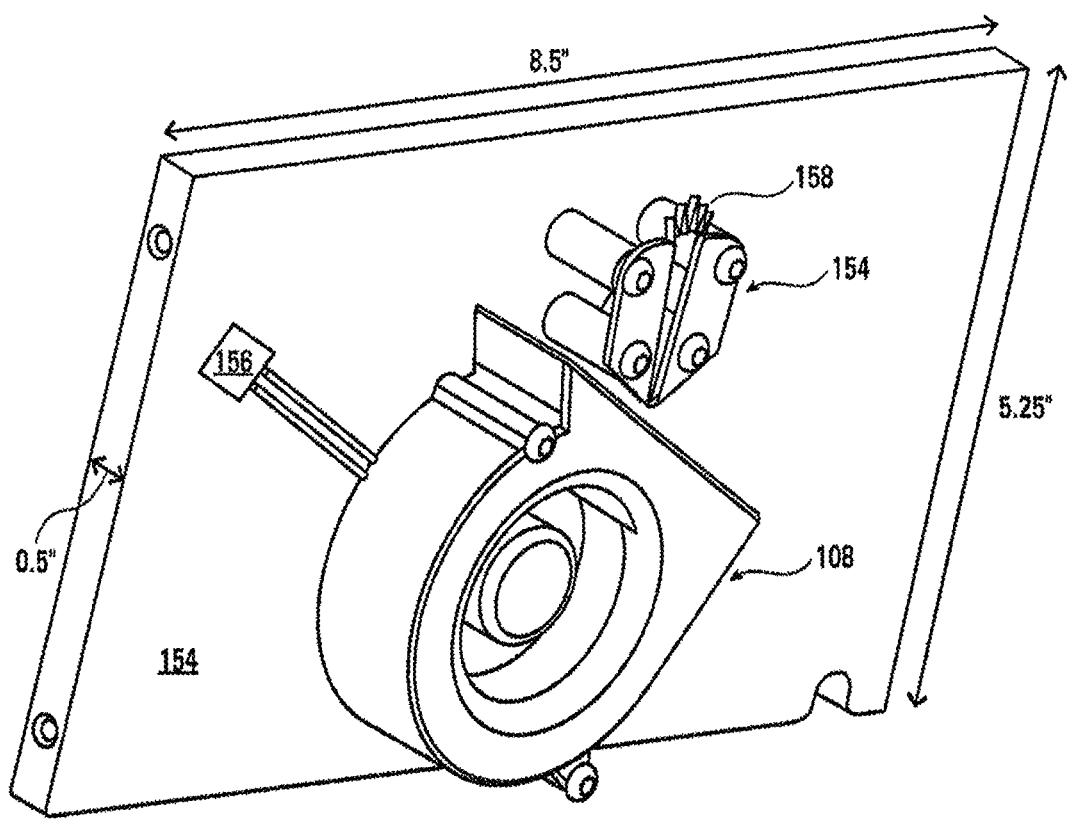
FIG. 8C is a schematic representation of a side perspective view of the gliding arc discharge similar to that illustrated in FIG. 1A hereof, and a blower disposed on a mounting plate for preventing the plasma from being extinguished by the flow of air through the disinfectant apparatus.

FIG. 8A is a schematic representation of the side view of another air disinfectant embodiment, 150, of the present invention, illustrating chamber, 152, containing at least one gliding arc discharge device, 154, through which air is directed by blower 108. Gliding arc discharge device 154 powered by power supply 12 disposed as part of power and control electronics, 156, generates plasma, 158. Air to be sterilized, 160, is filtered using pre-filter, 96, and drawn through chamber 152 by fan 94. Gliding arc discharge device 154 is mounted, along with blower 108, on ⅜"-0.5" thick PVC sheet, 161, and plasma 158 is not extinguished by air 160 since sheet 161 in conjunction with ⅜"-0.5" PVC baffle, 162, effectively shields plasma 158 from the affects of direct air flow. The NON-disinfected air is then purified by charcoal or carbon filter 100 to remove the plasma-generated NON-species, and released, 163. FIG. 8B is a schematic representation of the side view of the air disinfectant embodiment of the present invention shown in FIG. 8A hereof, illustrating some dimensions of the apparatus as constructed, while FIG. 8C is a schematic representation of a side perspective view of the gliding arc discharge similar to that illustrated in FIG. 1A hereof, and blower 108 disposed on mounting plate for preventing the plasma from being extinguished by the flow of air through the disinfectant apparatus. It should be mentioned that either of the gliding arc discharge apparatus illustrated in FIGS. 1A and 1B, and combinations thereof can be used in air purifier 150 in numbers necessary to handle the desired air flow.

Carbon or charcoal filter 100, is constructed of two carbon-coated polyester felts stacked together along with a MERV (Minimum Efficiency Reporting Values) 13 fabric. Pre-filter 96, electrode holder 161 are about 0.5" thick, and pre-filter 96 is typically MERV 6-8, its ability to capture larger particles (between 3 µm and 10 µm) being between about 50% and about 85% between these values.

Having described the general details of embodiments of the present invention, the following EXAMPLES provides additional details.

Example 1

Using the apparatus illustrated in FIG. 6C above, with and without activating smaller chamber 106 (Secondary Plasma), two colony forming units (CFU) of *Staphylococcus epidermis* of about ⅛ in. diameter were harvested from a tryptic soy agar plate. The harvested CFUs were dissolved in 2 mL of 0.1 M phosphate buffer solution (pH 7.3-7.4), vortexed until homogeneous, and diluted with distilled water to 1:1000 and 1:10,000. Five mL of the diluted inoculate was placed in a home air jet nebulizer (Compressor Nebulizer) and using the manufacturer's specifications, the particle sizes ranged from about 0.5 µm to 10 µm, at a nebulizing rate of about 0.25 mL/min., and an air flow of about 7 L/min. A "no plasma" control was run for each process condition. The total flow rate was controlled by vacuum pump 130 attached to the air impact monitor 134. The agar plates contained in the impact monitor were then incubated and counted.

Test results are shown in TABLE 1, where germ kill data result from a single pass (single turn) of air flow. The relative humidity of the incoming air was measured to be 59%, and the total air flow was measured at the exhaust of vacuum pump 130. For each sample, the nebulizer was operational for 180 s, after which air pumping was continued for 60 s, blower 108 being continuously operated. The impact plates were incubated for 20 h at 37° C., after which the CFUs were counted.

TABLE 1

| DILUTION | AIR FLOW (LPM) | PRIMARY PLASMA | SECONDARY PLASMA | CFU COUNT | % REDUCTION |
|---|---|---|---|---|---|
| 1000 | 10 | N | N | 3476 | |
| 1000 | 10 | Y | N | 156 | 95.5 |
| 1000 | 10 | N | Y | 466 | 86.6 |
| 1000 | 10 | Y | Y | 13 | 99.6 |

It is seen from TABLE 1 that the lowest efficacy was using only the Secondary Plasma, with the best efficacy being obtained when both plasmas were used.

Example 2

Air disinfection unit (ADU) 150 (FIG. 8A) was placed inside a clear plastic cube, 4' per side having an approximate volume of 1.812 m$^3$. Inoculum of Staph epidermidis was dispensed into the top of the cube using a syringe pump connected to a 120 kHz ultrasonic nozzle, which produced droplets having a mean diameter of about 18 µm. A mixing fan within the cube was continuously operated. Immediately after the inoculum was dispensed, ADU 150 was made operational. A sample pump mounted on the top of the cube withdrew about 10 Lpm of air at specific points in time. The impinger water samples were sent to an outside testing lab. Water samples were tested with a standard serial dilution/culture test, and the test results were in Colony Forming Units (CFU) per cubic meter of air.

TABLE 2 shows air disinfection data from ADU 150: log germ kill vs. air turns. Note that no germs were detected after 6 air turns. For this TABLE, fan 94 in FIG. 8A was operated at 95 CFM (2690 liters per min.). At this flow, the cube volume will experience one air turn in approximately 40 s. The data shows that the time to complete germ removal was on the order of 6 air turns, 240 s, or 4 min.

TABLE 2

| Air turns | log$_{10}$ CFU/m$^3$ |
|---|---|
| 0.0 | 5.60 |
| 2.0 | 5.60 |
| 4.0 | 5.30 |
| 6.0 | 0 |
| 10.0 | 0 |
| 17.8 | 0 |
| 22.3 | 0 |
| 35.5 | 0 |
| 44.5 | 0 |

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. Apparatus for surface sterilization comprising:
a first planar electrode having a chosen thickness and a straight edge having a chosen length, a first end, and a second end;
a second planar electrode having a chosen thickness, and a straight edge having a chosen length, a first end, and a second end, the straight edge of said second electrode opposing the straight edge of said first electrode, being spaced-apart and divergent therefrom, with the first end of said first electrode disposed a chosen distance from the first end of said second electrode, and the second end of said first electrode disposed at a larger distance away from the second end of said second electrode;
a high-voltage power source in electrical connection between said first electrode and said second electrode for providing a high voltage to said first electrode;
an air blower for providing a flow of air between the straight edge of said first electrode and the opposing straight edge of said second electrode;
an outer, air-tight chamber for enclosing said air blower, said outer chamber having an interior volume and one side with a flat portion, such that a first area of the flat portion is open and close to or in contact with said surface; and
an inner chamber disposed in the interior volume of said outer chamber for enclosing said first electrode and said second electrode, and having one side with a flat portion, such that a second area of the flat portion is open and close to or in contact with said surface within the first area;
whereby, air is circulated by said air blower from the interior volume of said outer chamber into said inner chamber, and a gliding arc plasma is generated near the first end of the straight edge of said first electrode and the first end of the straight edge of said second electrode by the high-voltage provided by said high-voltage power source, which moves between the straight edge of said first electrode and the opposing straight edge of said second electrode until it extinguishes, thereby increasing the concentration of products formed in the plasma.

2. The apparatus of claim 1, further comprising a gasket for sealing the open area of said outer chamber against said surface.

3. The apparatus of claim 1, further comprising a fan for evacuating the outer chamber, and a filter for removing the products formed in the plasma.

4. The apparatus of claim 3, wherein said filter is a charcoal filter.

5. The apparatus of claim 1, further comprising an atomizer for introducing water vapor into the plasma.

* * * * *